United States Patent [19]

Rausch et al.

[11] 4,228,007

[45] Oct. 14, 1980

[54] CHROMATOGRAPHIC CARTRIDGE AND HOLDER

[75] Inventors: Carl W. Rausch, Auburndale; Yury Tuvin, Newton; Uwe D. Neue, Framingham, all of Mass.

[73] Assignee: Waters Associates, Inc., Milford, Mass.

[21] Appl. No.: 1,540

[22] Filed: Jan. 8, 1979

[51] Int. Cl.² ............................................. B01D 15/08
[52] U.S. Cl. .................................. 210/198 C; 55/386; 210/251
[58] Field of Search ................. 210/31 C, 198 C, 350, 210/351; 55/386

[56] References Cited

U.S. PATENT DOCUMENTS

| | | | |
|---|---|---|---|
| 3,298,527 | 1/1967 | Wright | 55/386 |
| 3,387,630 | 6/1968 | Routson | 210/350 X |
| 3,453,811 | 7/1969 | Crowley | 55/386 |
| 3,687,287 | 8/1972 | Gwilliam | 210/350 X |
| 3,966,609 | 6/1976 | Godgille | 210/198 C |
| 4,059,523 | 11/1977 | Mochizuki et al. | 210/31 C |

Primary Examiner—John Adee

[57] ABSTRACT

A chromatography cartridge stabilized by radial compression is disclosed with integral distributors each composed of two abutting thin plates, one with generally radial slits and the other with radially-displaced apertures. Also disclosed are a replaceable filter cap which fits in the cartridge inlet and a holder for radially compressing the cartridge with pressure sequentially generated by pistons and applied across a flexible sleeve.

10 Claims, 8 Drawing Figures

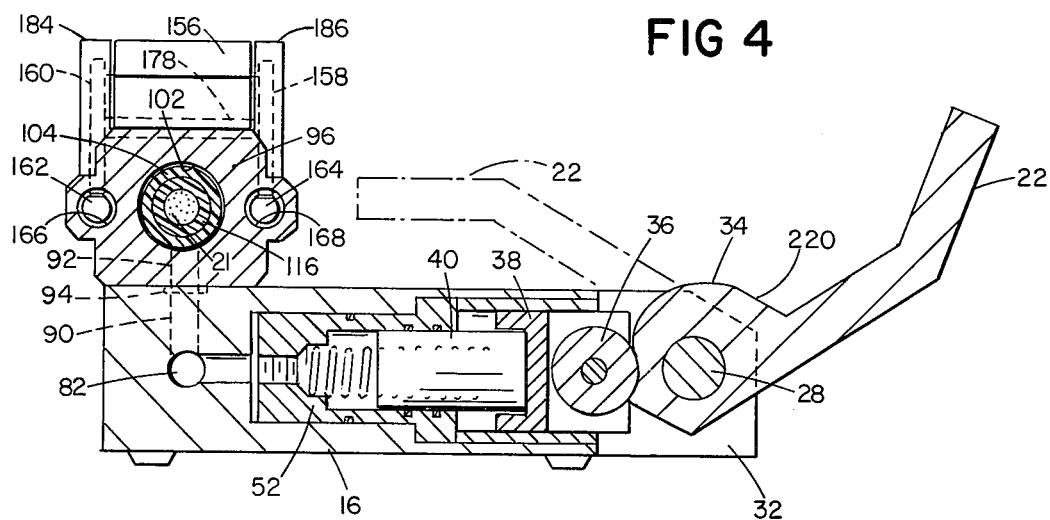
FIG 4
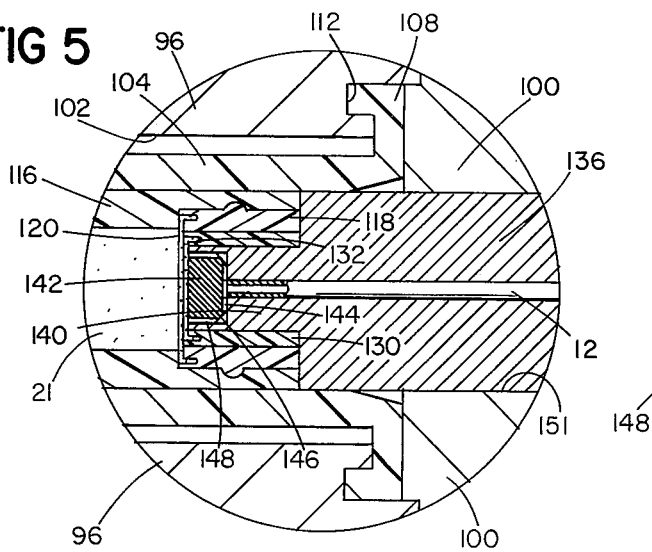
FIG 5
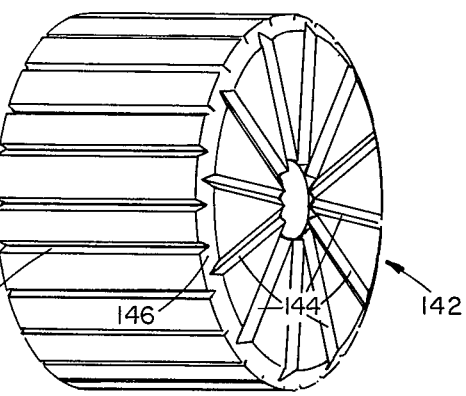
FIG 7
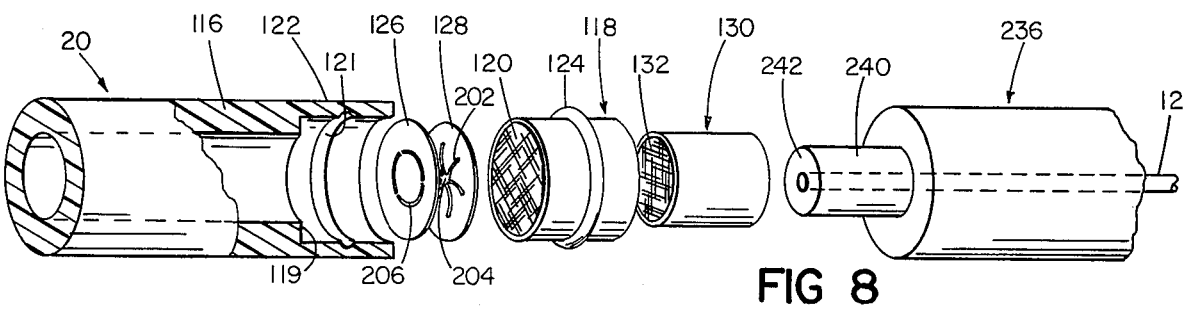
FIG 6
FIG 8

CHROMATOGRAPHIC CARTRIDGE AND HOLDER

FIELD OF THE INVENTION

This invention relates to chromatography.

BACKGROUND OF THE INVENTION

In chromatography, a test fluid in which a chemical sample containing numerous substances is dissolved is passed through a column of packing material contained in a tube. Because different substances in the sample have different affinities for the packing material, the time at which each substance emerges from the column will vary. The presence of a substance in the output fluid is generally detected by measuring changes in the physico-chemical properties of the fluid. A plot of these properties versus time will exhibit response peaks corresponding of each of the substances.

To improve resolution between response peaks, it is desirable to provide uniform flow paths for the test liquid through the column. Irregular-sized voids between particles in the packing material allow portions of the test liquid to advance ahead of others, thereby defeating the separation performed by the column and leading to an overlapping of the responses, so that resolution between response peaks is lost. Irregular-sized voids can occur within the packing and also at the interface between the packing and the tube wall.

The co-pending U.S. patent application of McDonald et al., Ser. No. 848,752, filed Nov. 4, 1977 (a continuation of Ser. No. 638,301, filed Dec. 8, 1975), entitled "Radial Compression of Packed Beds," both abandoned discloses eliminating irregular voids by radially compressing the packing material. Further, it discloses that voids between the packing material and the tube wall can be eliminated by deforming a plastic wall against the packing. The application discloses a variety of methods and apparatus for achieving radial compression and wall deformation. These include initial radial compression at the time of filling and further compression during use; using a plastic cartridge preexpanded with gas internally while filling and then compressed with gas externally during use; using a steel cartridge preexpanded by heating and pressurized slurry filling to provide permanent radial compression on contraction; using external compression pressures of between 10 and 1000 psi; and using cartridges with walls between 1 and 100 mils thick.

Another cause of degraded peak resolution is poor radial distribution of incoming and outgoing fluid. With cartridges that have substantial transverse dimensions relative to the size of the particles of the packing material (although the transverse dimension is generally much less than the longitudinal dimension), it is necessary to create a radially uniform flow profile through the cartridge. Simply allowing the fluid to enter and leave through small openings along the longitudinal axis causes overlapping of response peaks because fluid traveling along the longer radially outward paths takes a longer time to traverse the column than fluid traveling along the centerline.

There are commercially-available cartridges which provide radial distribution. A preparative chromatography cartridge (30 cm $\times$ 5 cm) sold by Waters Associates, Inc., uses a flat transverse plate with radially spaced holes; the holes communicate with a funnel chamber which moves the fluid between inlet and outlet conduits and the hole locations. A cartridge sold by Unimetrics Corporation under the Knauer trademark employs a thin plate inside the cartridge with radially-extending slits grouped in patterns of three so as to have the appearance of a bird footprint. Fluid moves radially in the slits while also flowing longitudinally through an abutting filter screen and then through a succession of fiber glass filters before reaching the packing material. In practice, mixing occurs in the series of filters, and peak resolution is thus degraded.

While both these cartridges distribute the fluid radially, neither they nor any others known have adequately eliminated another source of mixing, namely, regions of excessive volume within the distributor or the filter assembly. This excessive volume causes what is known as "outer column peak spreading" in which backmixing of separated substances occurs outside the column, resulting in poor resolution of response peaks.

A further source of degraded resolution is clogging of the filters provided at the inlet of the cartridges to retain the packing material. They can become clogged with foreign particles suspended in the test fluid. The above-mentioned Knauer cartridge can have its filter replaced but to do so requires removal of the cartridge retaining cap.

SUMMARY OF THE INVENTION

In its various aspects, the invention features: a chromatography cartridge having an integral distributor with radial transfer means (e.g., a thin plate with generally radially-extending slits) and a thin plate with radially-displaced apertures that communicate between the radial transfer means and the packing material, the plate apertures and the radial transfer means having a negligible volume in comparison to the cartridge (e.g., less than 0.1%), a replaceable filter cap placed in the inlet retention cap upstream of the retention screen, the filter assembly having a negligible volume in comparison to the cartridge; a plastic cartridge with snap-fit retention caps; a flow distributor with individual radially-extending passages for moving fluid radially and separate means for moving the fluid axially between ends of the radial passages and the packing material the distributor having a negligible volume in comparison to the cartridge; providing permanent radial compression of the packing material in a plastic cartridge by using pressurized slurry filling to expand the plastic wall and then allowing the wall to contract; radially compressing a plastic cartridge by surrounding it with a pressure-transmitting flexible sleeve and putting pressure on the sleeve; performing liquid chromatography while radially compressing the packing material with greater than 1500 psi (preferably between 2000–6000 psi) externally applied pressure; using pistons of different cross sectional areas to put radially-inward pressure on a cartridge, the areas being chosen so that operating force to successively actuate them be about the same; ejecting a cartridge from a cartridge holder by moving a pinion and through it a rack and pins to push on one end of the cartridge.

The invention provides a simple, rugged, relatively inexpensive, and improved chromatography cartridge. Permanent radial compression is provided by the plastic wall and pressurized slurry packing. The inner surface of the plastic wall conforms to the shape of individual particles. The cartridge is resistant to shock loads (mechanical, thermal, or chemical) which would destroy the packing in ordinary columns. The replaceable filter can be removed without removing the retention cap that retains the packing material and thereby disturbing the packing structure. The cartridge can be sealed in a simple manner to inlet and outlet end fittings by radial pressure on its ends. The distributor provides uniform radial distribution without also providing excessive mixing volume at the distributor. The integral plate distributor in the cartridge achieves distribution in minimum space and at low cost. Packing materials having a greater range of particle size distribution can be used with the same chromatographic efficiency.

The radial compression mechanism used in the cartridge holder is also simplified and improved. The greater external pressures (above 1500 psi) provided for radial compression improve uniformity in void size and thus improve resolution. The pressure-transmitting flexible sleeve allows application of external pressure without contact between the working liquid and the cartridge. Pressure for radial compression can be applied manually by the piston arrangement, and the ejection mechanism makes for easy removal of the cartridge, all of which simplifies operation.

PREFERRED EMBODIMENTS

We turn now to description of the structure, manufacture, and operation of preferred embodiments of the invention, after first briefly describing the drawings.

DRAWINGS

FIG. 4 is a cross-sectional view at 4—4 of FIG. 2, showing a cross section of the cartridge and illustrating operation of one pressurizing arm.

FIG. 5 is an enlarged longitudinal cross-sectional view at 5—5 of FIG. 1, showing the chromatography cartridge within the holder.

FIG. 6 is a longitudinal cross-sectional view of a preferred embodiment of the chromatography column.

FIG. 7 is a perspective view of the distributor head of a preferred embodiment, with flow grooves shown enlarged.

FIG. 8 is an exploded perspective view of another preferred cartridge embodiment, showing an integral distributor in the column and the silica packing removed.

STRUCTURE

Figure 1:
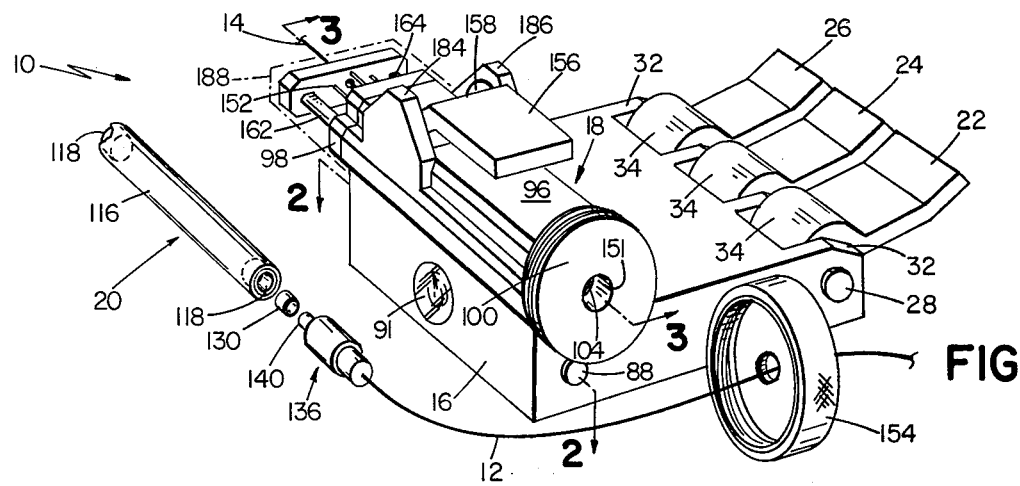
FIG. 1 is a perspective view of the cartridge holder.

Referring to FIG. 1, there is shown chromatography cartridge holder 10 with replaceable chromatography cartridge 20 removed. Sample liquid enters through inlet tube 12 (9 mil I.D.) and exits through outlet tube 14 (9 mils I.D). Holder 10 consists of base 16 in which pistons for pressurization are contained and cartridge chamber 18 in which replaceable cartridge 20 is radially compressed. Packing material 21 (spherical silica; 5–15 micron) is contained within cartridge 20.

Figure 2:
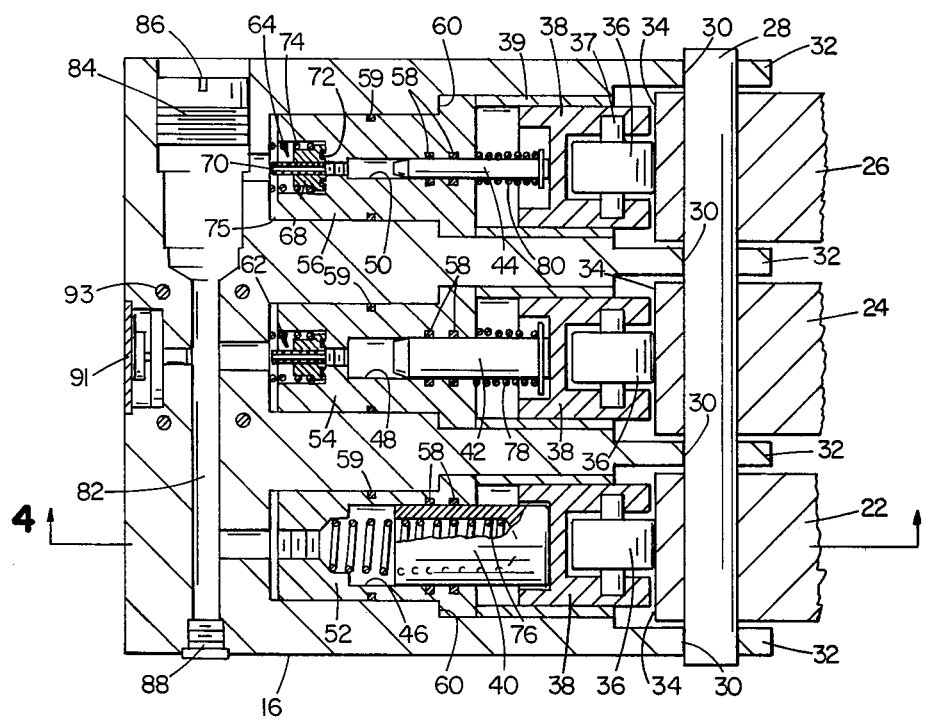
FIG. 2 is a cross-sectional view at 2—2 of FIG. 1, showing the cartridge holder unpressurized and outboard portions of the pressurizing arms broken away.

Three pressurization arms 22, 24, 26 are pivotally supported on shaft 28 which extends through coaxial holes 30 in arm supports 32 of base 16 (FIG. 2). Nylon bushings and washers and steel spring washers (not shown) provide friction for arms 22, 24, 26 on shaft 28. Each arm has camming surface 34 at its base (FIG. 4). The camming surfaces act against steel rollers 36 supported by shafts 37 on internal hard-coated aluminum guides 38. The guides ride within bushings 39 (oil impregnated bronze) held in bores of base 16 by retaining rings (not shown). Guides 38 act against pistons 40, 42, 44 which slide within bores 46, 48, 50 of bronze cylinders 52, 54, 56. O-rings 58 seal between the pistons and bores. O-rings 59 seal between the cylinders and base 16. Cylinders 52, 54, 56 seat against shoulders 60. Piston 40 has a ¾ inch working diameter; piston 42 a ⅜ inch diameter; piston 44 a 3/16 inch diameter. Flow restriction valves 62, 64 are supported between cylinders 54, 56 downstream of pistons 42, 44. Each valve includes a moveable member 68, a small diameter flow passage 70 in moveable member 68, a gasket 72 for sealing between cylinders 54, 56 and member 68, and a spring 74 compressed between a shoulder 75 of base 16 and member 68. Piston 40 and cylinder 52 do not have a flow restriction valve downstream. Return springs 76, 78, 80 between each piston and cylinder are preloaded to return the pistons to their starting positions.

Figure 3:
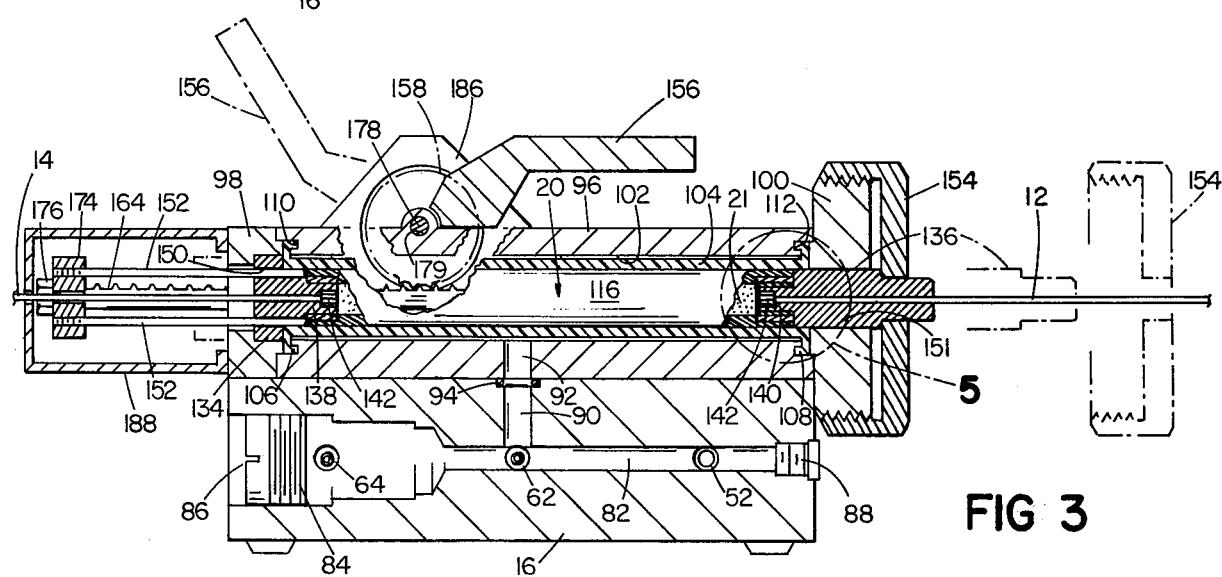
FIG. 3 is a cross-sectional view at 3—3 of FIG. 1, showing the chromatography cartridge within the holder and illustrating operation of the ejection mechanism.

Branch conduits connect the outlets of each piston and cylinder to central conduit 82. Adjustment plug 84 on one end of conduit 82 has an externally accessible slot 86 which is rotated to adjust the internal volume of the device. Cap 88 seals the opposite end of conduit 82. Vertical conduit 90 connects base 16 to cartridge chamber 18 (FIG. 3). Pressure gauge 91 communicates with conduit 82.

Referring to FIGS. 3 and 4, vertical conduit 92 in chamber 18 is a continuation of conduit 90. O-ring 94 seals the conduits at the interface between base 16 and chamber 18. Four cap screws 93 (FIG. 2) fasten chamber 18 to base 16. Chamber 18 consists principally of pressurizing cylinder 96, end caps 98, 100, and a cartridge ejection mechanism. Conduit 92 communicates with pressurizing bore 102 in cylinder 96. Flexible sleeve 104 (Viton rubber) is mounted within bore 102. Lips 106, 108 of sleeve 104 fit into annular grooves 110, 112 at axial ends of cylinder 96. End caps 98, 100 are secured to cylinder 96 by cap screws (not shown). No seals other than rubbery sleeve 104 are required for sealing between the end caps and the cylinder.

Supported within flexible sleeve 104 is replaceable chromatography cartridge 20, shown removed from the holder in FIGS. 1 and 6. The cartridge consists of a high density polyethylene cylinder 116 (0.525 inch outside diameter and 0.100 inch thick walls) and retention caps 118 with integral filter screens 120 (2 micron apertures). Caps 118 are retained in cartridge 114 by cooperation between annular grooves 121 in narrow-wall end portions 122 and annular protrusions 124 in the caps. Replaceable filter cap 130 with integral second filter screen (2 micron apertures) 132 is inserted inside the input retention cap.

Cartridge 20 fits closely within flexible sleeve 104, (FIGS. 3 and 5) and abuts output fitting 134 at one axial end, and input fitting 136 at the other end. Fittings 134, 136 have male portions 138, 140 which fit tightly within the mating female portions of retention cap 118 on one end and filter cap 130 on the other end. Inlet and outlet tubes 12, 14 are received within fittings 134, 136. The tubes communicate at their ends with distributor heads 142 (shown enlarged in FIG. 7) which radially transfer fluid from the tube to radially spaced locations in the cartridge at the input end and vice versa at the output.

Referring to FIG. 7, radially direct grooves 144 (twelve shown, but eight preferred) move the fluid radially, chamfer 146 in cooperation with the internal shoulders of fittings 134, 136 moves the fluid circumferentially, and twenty-four axial grooves 148 move the fluid axially. The ends of groove 148 communicate with filter screens in cartridge 114. Grooves 144, 148 are about 3 mils wide, and distributor heads 142 are 0.20 inches in diameter. Outlet fitting 134 has four holes 150 for receiving ejection pins 152 and is retained by end cap 98. Inlet fitting 136 slips through hole 151 in end cap 100 and is retained by removable cap 154, which threads onto external threads of end cap 100.

The ejection mechanism includes ejection handle 156, pinion gears 158, 160 fastened to each side of the handle, racks 162, 164 sliding within bores 166, 168 in cylinder 96 and through holes in end cap 98 and secured to bracket 174 by nuts 176, and ejection pins 152 secured in bracket 174. Pinions 158, 160 and handle 156 rotate on shaft 178 which is supported in holes 179 in cylinder 96. Vertical members 184, 186 integral with cylinder 96 cover pinions 158, 160. Plastic cover 188 is mounted over the exposed portions of racks 162, 164.

Referring to FIG. 8, there is shown another preferred embodiment of the invention. In place of distributor heads 142, flow distribution plates 126, 128 are inserted at each end of cartridge 20 between retention caps 118 and shoulders 119. Radial distribution plates 128 abut filter screens 120 and have curved slits 202 radially extending from central hole 204. Plates 126 contact packing 21 and have three arcuate slits 206 positioned at the same radial location (0.20 inch diameter) as grooves 148 in distributor heads 142. Tubes 12, 14 extend flush with inward face 242 of male portion 240 of inlet fitting 236 so as to communicate through the thin filter screens with central hole 204 in plate 128. The outlet fitting (not shown) similarly has outlet tube 14 brought flush with its inward face.

MANUFACTURE

Cartridge holder 10 is built following conventional manufacturing methods.

Cartridge 20 is filled with silica packing material 21 by passing through it a slurry of silica suspended in a pressurized low-viscosity liquid (e.g., Freon or methanol). One retention cap 118 and distributor plates 126, 128 are installed during filling and they trap silica while allowing the liquid to pass. After the cartridge is full, pressure from the liquid is removed, and wall 116, which was expanded during pressurized filling, contracts to permanently radially compress the silica. Excess silica at the inlet is then removed, and the second retention cap 118, distributor plates 126, 128, and filter cap 130 are installed.

OPERATION

To operate the chromatography cartridge holder, replaceable cartridge 20 is inserted within rubbery sleeve 104 by unscrewing removeable cap 154, inserting male portion 140 of inlet fitting 136 within the well formed by filter cap 130, and pushing the cartridge into sleeve 104 using fitting 136 as a handle. Cap 154 is then screwed onto end cap 100 to complete the insertion.

Pressure is applied around sleeve 104 to radially compress cartridge 114 by sequential operation of pressurizing arms 22, 24, 26; arm 22 raises the pressure to about 600 psi, arm 24 to about 1600 psi, and arm 26 to about 2200 psi. Cam surfaces 34 have straight portions 220 which retain each arm in the pressurizing position. Rotation of each handle between the positions illustrated in FIG. 4 causes cam surfaces 34 to push against rollers 36 and thereby move guides 38 inward against one of pistons 40, 42, 44. The areas of pistons 40, 42, 44 are selected to equally divide operating forces between the three handles. Operation of arm 22 and associated piston 40 displaces the greatest volume of glycerin. This initial large displacement moves sleeve 104 tightly against cartridge 114, and begins compression of the silica within the column. Operation of handles 26, 28 continue compression of the silica. Pistons 42, 44 are progressively smaller owing to the nonlinear (approximately exponential) compression characteristics of the silica and surrounding polyethylene wall 116 and rubbery sleeve 104.

During pressurization, flow restriction valves 62, 64 at the outlet of pistons 42, 44 provide no substantial flow restriction. Increasing pressure moves moveable member 68 away from body 66, compressing spring 74 and opening a wide flow passage between member 68 and body 66, past gasket 72.

Glycerin is sealed within chamber 18 by cooperation between lips 106, 108 on rubbery sleeve 104 and annular grooves 110, 112 in cylinder 96. Pressurization of the glycerin forces lips 106, 108 tightly against the radially outermost walls of grooves 110, 112, preventing the glycerin from flowing between the walls and the lips. Sleeve 104 also provides radially compressive forces on end portions 122 of cartridge 114 to seal the cartridge to inlet and outlet fittings 140, 138. The radially inward forces squeeze end portions 122, retention caps 118, and filter cap 130 against each other and against male portions 138, 140 of fittings 134, 136, thereby sealing all possible outward fluid paths from tubes 12, 14 and the interior of cartridge 114.

When arm 26 has been moved into its pressurizing position, cartridge 20 is fully radially compressed and chromatography can begin. Test liquid is pumped under pressure into cartridge 20 through inlet tube 12, and emerges through outlet tube 14, which is connected to a detector (not shown) to measure solute concentrations.

If sufficient foreign particles enter through inlet tube 12 to clog filter screen 132 of filter cap 130 the cartridge may be removed, and the filter cap cleaned or replaced.

To remove cartridge 20, arms 22, 24, 26 are moved to their open position (shown in FIG. 1) in the reverse sequence used for pressurization—arm 26 first and arm 22 last. Flow restriction valves 62, 64 slow travel of pistons 42, 44 to prevent operator injury. Moveable members 68 press against gaskets 72, and fluid returns through small-diameter flow passages 70. When arm 22 is released, spring 76 moves piston 40 back beyond the zero-pressure position, thereby creating a below atmospheric pressure at pressurizing bore 102 to pull sleeve 104 away from cartridge 20.

After pressure is removed, cartridge 20 is ejected by unscrewing cap 154 and rotating ejection handle 156 to the position shown in phantom in FIG. 3. This rotates pinions 158, 160, and through them moves racks 162, 164 and ejection pins 152. The pins, which extend through holes 150 in outlet fitting 134, press against the outlet end of cartridge 20, and move it axially to the location shown in phantom. From this half withdrawn position, the cartridge is removed manually.

To minimize upstream-downstream concentration mixing in the cartridge and accompanying peak spreading in the output, test fluid entering through inlet tube 12 and exiting through outlet tube 14 is broken into a plurality of separate radially displaced streams by distributor heads 142 (FIGS. 5 and 7). The separate streams enter and leave the cartridge through axial grooves 148 in distributor heads 142. The internal volume of the distributor is less than about 3 to 5 microliters, and the fluid paths are short, thereby minimizing upstream-downstream mixing in the distributor. The 0.20 inch diameter of heads 142 positions axial grooves 148 at a radial location which divides the cartridge cross section into an inner circle and an outer ring, each with approximately the same area. By so distributing the fluid, each successive volume segment of incoming fluid in inlet tube 12 is spread uniformly across the cross section of cartridge 114, is moved through the cartridge all at substantially one axial location, and is removed from the cartridge by being transferred to substantially one axial location in outlet tube 14. Without proper distribution of the incoming and outgoing flow, a given axial volume segment of incoming fluid would, due to initial outward radial spreading upon entry into the cartridge, move through the cartridge at axial locations that differ radially in a curved profile, with radially outward portions trailing portions moving through the center. When such a curved profile is removed from a cartridge, upstream-downstream mixing and accompanying peak spreading necessarily results.

In the other preferred embodiment shown in FIG. 8, the radial flow passages are defined by slits 202 and the abutting surfaces of plate 126 and filter screen 120. Face 242 of distributor 236 presses tightly against filter screens 120, 132 to keep fluid within slits 202. Arcuate slits 206 axially transfer the radially displaced fluid to the packing material.

To avoid additional upstream-downstream concentration mixing in fittings 134, 136, and the other fluid connections to the cartridge, flow volume within the fittings and connections is minimized. In both distributor embodiments (FIGS. 7 and 8), fluid traveling in tubes 12, 14 is divided abruptly into a plurality of small flow channels which are then routed to the desired radial locations. Further, filter screens 120, 132 are made of thin stainless steel mesh to minimize their volume. In distributor head 142 (FIG. 7), the small flow channels are defined by the individual radial grooves 144, chamfer 146, and individual axial grooves 148. In the other preferred cartridge embodiment (FIG. 8), the flow channels are defined by the radial slits and arcuate slits. The high radial compression pressures tend to make the interior surface of polyethylene wall 116 of cartridge 20 conform to the shape of the silica particles, thus eliminating "wall channeling" wherein voids at the wall allow unevenly fast advance of the test liquid there. Experiments have observed that after compression impressions are left by the silica particles on the interior surface of wall 116.

The 0.100 inch thickness of wall 116 provides sufficient handling rigidity outside of holder 10 while also providing sufficient expansion during pressurized fill to give small but permanent radial compression to the silica.

Other embodiments of the invention will occur to those skilled in the art. For example, the cartridge wall thickness can be varied between about 0.005 and 0.250 inches; and the number of radially directed grooves in distributor heads 142 could be fewer or greater than eight. Further, there are many variations possible on the arrangement of plates 126, 128 in FIG. 8. For example, the radial flow distribution function of radially slit plate 128 could be performed, without the plate, by filter screen 120 or screen 132. Fluid would move radially within the filter mesh. Or the radial distribution could be achieved by moving plate 126 adjacent to face 242 and providing a small volume gap between face 242 and plate 126. In any of these variations it is, however, necessary to keep the flow volume inside the distributor small compared to the cartridge volume.

A most-preferred production model of the cartridge holder includes several small variations from the holder described above and shown in FIGS. 1 through 5. Cylinder 96 and base 16 are made from a single casting, eliminating the need for fasteners 92 and seal 94. Gauge 91 is moved to the face of base 16 on which plug 88 is located. Pinion covers 184 are rectangular rather than trapezoidal.

In a most-preferred cartridge embodiment, the location of plates 126, 128 is shifted from that shown in FIG. 8 to a location between the filter screens and face 242.

What is claimed is:

1. Apparatus for radially compressing the wall of a chromatography cartridge containing chromatographic packing material, said apparatus comprising:

means for introducing the chromatographic fluid to the inlet of said cartridge, means for removing the chromatographic fluid from the outlet of said cartridge, chamber means surrounding said wall of said cartridge, pressure generating means communicating with said chamber means, said pressure generating means including a plurality of pistons of different working areas,
said working areas being selected to make the forces required to move said pistons substantially equal when the pistons are moved in order of descending working area, a plurality of cylinders in which said pistons move, means for sequentially moving said plurality of pistons, and conduits connecting the high pressure sides of said pistons to said chamber, whereby when said apparatus is filled with working fluid, said means for moving said pistons may be operated to raise in stages the pressure in said chamber and thereby reach the desired pressure for radially compressing said cartridge with lower forces applied to said pistons than would otherwise be required.

2. The apparatus of claim 1 wherein said means for sequentially moving said pistons includes manually-operable arms moveable between a rest position and a pressurizing position, cam surfaces moveable by said arms, and cam follower means contacting said cam surfaces and actuating said pistons, whereby the different working areas of said pistons substantially equalize the operating forces required to move said arms between positions, thereby reducing the maximum operating force required.

3. The apparatus of claim 2 further comprising spring means for returning said pistons to their unpressurizing position when said arms are returned to their rest position and flow restriction means in at least one of said conduits connecting said pistons to said chamber, said flow restriction means only restricting flow moving away from said chamber toward said pistons, whereby when said arms are moved to their rest positions, said pistons are moved to the unpressurizing position by said springs and said flow restriction means damps the return movement of some of said arms.

4. The apparatus of claim 3 wherein said flow restriction means are in all conduits except the conduit connected to the piston having the largest working area and the spring means associated with said largest-area piston includes means for moving said piston beyond the zero-pressure position when the associated arm is in the rest position, thereby creating a vacuum in said chamber to facilitate removal of said cartridge.

5. Apparatus for radially compressing the wall of a chromatography cartridge containing chromatographic packing material, said apparatus comprising:

means for introducing the chromatographic fluid to the inlet of said cartridge, means for removing the chromatographic fluid from the outlet of said cartridge, chamber means surrounding said wall of said cartridge, pressure generating means communicating with said chamber means, and ejection means for removing said cartridge from said apparatus, said ejection means including pin means extending along the axial direction of said cartridge and positioned to abut one axial end of said cartridge and rack and pinion means for axially translating said pin means.

6. The apparatus of claim 5 wherein said rack and pinion means includes two transversely spaced axially extending racks on either side of said cartridge, guiding means for supporting and guiding said racks during their axial travel, bracket means connecting said racks to each other and to said pin means, and two transversely spaced pinions engaged with said racks and said apparatus further includes a handle mounted for rotation on the axis of rotation of said pinions and fastened to said pinions, whereby rotation of said handle rotates said pinions and translates said racks and pins, thereby exerting an axial force on said one end of said cartridge to eject it from said apparatus.

7. A cartridge for chromatography, said cartridge containing chromatographic packing material and comprising:

a tubular body, said body having a flexible plastic wall capable of being radially expanded when subjected to the internal pressure arising during slurry packing of said packing material and of being radially compressed when subjected to external compression pressures during use, integral plastic end portions each having a cylindrical recess open at the end of the cartridge and an annular groove around the interior cylindrical surface of said recess, and retention caps secured in said end portions, each said cap comprising a tubular member, an annular ridge on said member adapted to be received by said annular groove in each said end portion, and a thin transversely oriented filter screen secured to said member, whereby said packing material is contained within said cartridge and is permanently radially compressed by said plastic wall after slurry packing pressure is removed, whereby said filter screens axially retain said packing material inside said cartridge, whereby said retention caps can be snapped into place in said end portions of said cartridge by applying axial force to said caps sufficient to snap said ridge into said groove, and whereby said cartridge may be sealed to inlet and outlet tubes carrying fluid chromatography samples by applying radial compression to said integral end portions, thereby squeezing said end portions and retention caps inward against a male fitting which may be inserted in said retention caps.

8. The cartridge of claim 7 further comprising a removeable filter cap, said filter cap including a tubular member having a cylindrical exterior surface dimensioned to fit tightly within the interior cylindrical surface of said tubular member of one said retention cap and a thin transversely oriented filter screen secured to one end of said tubular member, whereby said filter cap can be inserted in one said retention cap with its filter screen abutting said filter screen of said retention cap, whereby said filter cap can be removed and replaced when the pores of its filter screen have become clogged with particles, and whereby radial compression of a said end portion of said cartridge against a male fitting which carries the inlet tube and which may be inserted inside said filter cap will seal all the cylindrical interfaces between the fitting, filter cap, retention cap, and end portion, thereby providing a fluid-tight seal between the inlet tube and the cartridge.

9. A cartridge for chromatography, said cartridge containing chromatographic packing material and comprising:

a tubular body, said body having a flexible plastic cylindrical wall capable of being radially compressed inward during use, retention caps at either end of said tubular body for axially retaining said packing material, said caps including a filter screen in contact with said packing material, and a removeable filter cap, said filter cap including a tubular member having a exterior surface dimensioned to fit tightly within the interior cylindrical surface of said retention caps and a thin transversely oriented filter screen secured to one end of said tubular member, whereby said filter cap can be inserted in one said retention cap with its filter screen abutting said filter screen of said retention cap and whereby said filter cap can be removed and replaced when the pores of its filter screen have become clogged with particles, without having to remove said retention cap and thereby expose said packing material.

10. The cartridge of claim 9 wherein said exterior surface of said filter cap and said interior surface of said retention cap are cylindrical.

* * * * *

UNITED STATES PATENT AND TRADEMARK OFFICE
CERTIFICATE OF CORRECTION

PATENT NO. : 4,228,007

DATED : October 14, 1980

INVENTOR(S) : Carl W. Rausch et al.

It is certified that error appears in the above–identified patent and that said Letters Patent are hereby corrected as shown below:

Column 9, line 62, "internal pressure arising" is changed to --internal pressures arising--.

Column 12, line 3, "claim 9" is changed to --claim 8--.

Signed and Sealed this

Twenty-seventh Day of January 1981

[SEAL]

Attest:

RENE D. TEGTMEYER

Attesting Officer      Acting Commissioner of Patents and Trademarks